US010492893B2

(12) United States Patent
Van Der Poel et al.

(10) Patent No.: US 10,492,893 B2
(45) Date of Patent: Dec. 3, 2019

(54) TIP FOR AN OPTICAL SCANNER (71) Applicant: 3SHAPE A/S, Copenhagen K (DK)

(72) Inventors: Mike Van Der Poel, Rødovre (DK);
Casper Rasmussen, Frederiksberg (DK); Finn Hansen, Greve (DK);
Søren Greve Jensen, Vemmelev (DK)

(73) Assignee: 3SHAPE A/S, Copenhagen K (DK)

( * ) Notice: Subject to any disclaimer, the term of this patent is extended or adjusted under 35 U.S.C. 154(b) by 558 days.

(21) Appl. No.: 15/060,098

(22) Filed: Mar. 3, 2016

(65) Prior Publication Data

US 2016/0256245 A1    Sep. 8, 2016

(30) Foreign Application Priority Data

Mar. 3, 2015  (DK) .......................... PA 2015 70116

(51) Int. Cl.
| | |
|---|---|
| *A61B 1/12* | (2006.01) |
| *A61B 1/05* | (2006.01) |
| *A61B 1/00* | (2006.01) |
| *A61C 9/00* | (2006.01) |
| *A61B 1/253* | (2006.01) |
| *G01B 21/04* | (2006.01) |
| *A61C 1/16* | (2006.01) |

(52) U.S. Cl.
CPC ........ *A61C 9/0053* (2013.01); *A61B 1/00096* (2013.01); *A61B 1/00101* (2013.01); *A61B 1/00177* (2013.01); *A61B 1/053* (2013.01); *A61B 1/121* (2013.01); *A61B 1/253* (2013.01); *A61C 1/16* (2013.01); *G01B 21/047* (2013.01)

(58) Field of Classification Search
CPC ..... A61C 9/0053; A61C 1/16; A61B 1/00096; A61B 1/00101; A61B 1/00177; A61B 1/053; A61B 1/121; A61B 1/253; G01B 21/047

USPC ........ 600/108, 109, 114, 117, 118, 127, 129, 600/157, 160, 169, 175, 176, 182
See application file for complete search history.

(56) References Cited

U.S. PATENT DOCUMENTS

| | | | |
|---|---|---|---|
| 3,971,954 A | 7/1976 | Kleinberg et al. | |
| 8,360,771 B2* | 1/2013 | Stookey ............. | A61B 1/00041 433/29 |
| 2002/0085773 A1* | 7/2002 | Shoda ..................... | F16C 19/36 384/47 |
| 2005/0003323 A1 | 1/2005 | Katsuda et al. | |
| 2014/0128679 A1 | 5/2014 | Wieters | |
| (Continued) | | | |

FOREIGN PATENT DOCUMENTS

| | | |
|---|---|---|
| JP | 2013-092478 A | 5/2013 |
| WO | WO 99/42054 A1 | 8/1999 |
| WO | WO 2013/132091 A | 9/2013 |

OTHER PUBLICATIONS

Danish Search Report for Application No. PA 2015 70116 dated Oct. 8, 2015.

*Primary Examiner* — Timothy J Neal
*Assistant Examiner* — William B Chou
(74) *Attorney, Agent, or Firm* — Buchanan Ingersoll & Rooney P.C.

(57) ABSTRACT

Disclosed is a tip for an optical scanner, where said tip comprises a framework and an optical element. For some configurations the optical element is releasable attaching to the framework by a holding means of the tip. For some configurations the tip framework is formed in two materials of different thermal conductivities.

15 Claims, 7 Drawing Sheets

(56) References Cited

U.S. PATENT DOCUMENTS

2015/0018613 A1\* 1/2015 Hollenbeck ........ A61B 1/00096
600/109
2015/0079535 A1 3/2015 Hollenbeck et al.

\* cited by examiner

TIP FOR AN OPTICAL SCANNER

This invention generally relates to scanners, such as 3D scanners for intra-oral scanning. More particularly, the invention relates to a tip for an intra-oral scanner.

BACKGROUND

Intra-oral scanners are often designed to have a tip and a main body, where the tip enters the patient's mouth during a scanning and several components of the scanner, such as light source and image sensor, are placed in the main body. Examples of commercially available intra-oral scanners include the 3shape TRIOS, the Cadent Itero and the Sirona CEREC intra-oral scanners.

When used for intra-oral scanning a scanner and especially its tip which must be cleaned after use to avoid the risk of transferring diseases from one patient to another. WO2013132091 describes a tip for an intra-oral scanner where a mirror provides that the probe light from a light source in the main body of the scanner is projected onto the scanned object and light returning from the scanned object is projected onto the image sensor in the main body. The tip can be removed from the main body of the scanner and can be cleaned by autoclaving such that the tip can be reused without risk of transferring e.g. bacteria from one patient to the next.

SUMMARY

Disclosed is a tip for an optical scanner, wherein said tip comprises:
  a framework;
  an optical element; and
  a holding means for releasable attaching the optical element to the framework.

In the context of the present invention the phrase "releasable attached" refers to situations where two units temporarily can be attached to one another and can be separated from each other again without use of excessive force and/or without destroying or altering the units. For example an optical element can be said to be releasable attached to a tip framework when it can be removed from the framework again without use of excessive force.

Having an optical element which is releasable attached in the tip provides several advantages over designs with a permanent attachment of the optical element on the tip framework.

For example, the optical element and the framework can be cleaned using different cleaning methods. Optical element are often not capable of withstanding the aggressive cleaning methods preferably applied to the tip framework and a more gentle cleaning must be applied in to the optical element order to ensure that it can be reused in the scanner tip. Using a releasable attachment of the optical element to the framework thus has the advantage that the optical element easily can be removed from the framework after a scanning and be exposed to a separate cleaning procedure before it is attached to the framework again for scanning the next patient.

Further, the framework and the optical element can be replaced independently such that replacement of the entire tip is not required when only one part needs to be replaced.

Examples of permanent attachment is when two parts are attached to each other by gluing or welding. For example a tip which is permanently attached to the main body of a scanner cannot be removed from the main body without destroying at least part of the tip and/or main body.

In some embodiments, the holding means comprises a first part permanently attached to the framework and a second part permanently attached to the optical element.

A releasable attachment of the second part of the holding means to the first part then provides a releasable attachment of the optical element to the tip framework via the holding means.

In some embodiments, the first and/or second part comprises a magnetic material such that magnetic interaction between the first and second part provides for the releasable attachment of the optical element to the framework.

In some embodiments, the magnetic material is comprised in one of said first and second parts and the other of said first and second parts comprises a magnetizable material which is magnetized when the first and second parts are brought together. This provides that the magnetic interaction between the first and second parts is generated when the parts are brought together. The optical element is thus attached to the tip via the magnetic interaction between the magnet material and the magnetized material. The first part may be the one comprising the magnetic material while the second part may be the one comprising the magnetized material, and vice versa. The magnetizable material may be weakly magnetic even before being brought into contact with the magnet, which often is the case for e.g. stainless steel.

In the context of the present application, the phrase "brought together" may refer to the situation where the second element is brought into close proximity with the first element, such as in contact with the first element.

In some embodiments, the first and second parts of the holding means are both permanent magnets permanently attached to the framework and optical element, respectively. The permanent magnets are arranged on the framework and optical element in such a manner that the magnets attract each other when the optical element is arranged according to its planned placement on the tip framework.

Magnetic holding of the optical element has the advantage that the holding means and the tip framework can be designed such that all surfaces are easily accessible to e.g. high-level disinfectants used for cleaning.

The strength of the magnetic interaction is adjusted to provide that the optical element is securely attached to the framework when the scanner and tip is in use, and to provide that an operator can release the optical element without applying excessive force.

In some embodiments, the holding means comprises a constriction, such as a slit, adapted for holding the optical element, such that the optical element is releasable attached to the framework when arranged in said constriction.

The constriction and the optical element are preferably shaped such that an operator must apply some force to release the optical element from the constriction. For example the width or height of a slit constriction can be equal to the corresponding dimension of the optical element. Or when the material in which the constriction is defined is a slightly flexible material, the width or height of the constriction can be slightly smaller than the corresponding dimension of the optical element such that the optical element must displace the material providing for a firm releasable attachment of the optical element to the framework of the tip.

In some embodiments, the constriction comprises a first opening allowing the optical element to enter the constriction and a second opening distal to the first opening.

In some embodiments, the dimensions of said second opening and of the optical element is such that the height and/or thickness of the optical element exceeds the corresponding height and/or thickness of the second opening. Preferably the optical element can be accessed through the second opening such that a push can be applied to the optical element though the second opening. This can make removal of the optical element from the constriction easier compared to situations where it must be pulled out of the constriction. Further the second opening can act as an indicator showing weather the optical element is arranged correctly in the constriction.

In some embodiments, the holding means comprises one or more confining structures arranged to restrict movement of the optical element.

The one or more confining structures can assist the other units of the holding means in holding the optical element in its correct place on the tip framework.

In some embodiments, the one or more confining structures restrict the movement of the optical element in the plane of the surface of the framework onto which the optical element is releseably attached. For example, when the optical element is attached to a second part of a magnetic holding means which is held by magnetic interaction with a first part attached to a surface of the tip framework, the optical element may still slide along the plane of contact between the first and second parts. The one or more confining structures are then preferably arranged to confine the movement of the second part and the optical element in the plane of contact, such that these cannot slide to a point where the displacement of the optical element presents a problem for the optical system of the scanner or to a point where first and second parts of the magnetic holding means no longer are held together by the magnetic interaction and the optical element detaches from the framework.

In some embodiments, the one or more confining structures comprise one or more stops and/or a surface or an edge of the framework.

In some embodiments, the optical element comprises a mirror.

In some embodiments, the optical scanner is a 3D scanner for recording topographic characteristics of a surface of at least part of a body orifice, such as an intra-oral scanner.

In some embodiments, the framework comprises a proximal end for entering the body orifice, where the proximal end comprises a first portion made in a first thermal conductive material, where the optical element is arranged at said first portion in thermal contact with the first thermal conductive material either directly or via the holding means.

A distal end of the tip is preferably made at least partly in a thermal insulating material and is preferably configured for being mounted on a tip-supporting portion of a main body of the 3D scanner.

In some embodiments, the tip is configured for being releasable attached to a mounting part of the optical scanner.

Such a releasable attachment of the tip can be realized by shaping the tip framework and the mounting part of the scanner body such that the tip can slide onto the mounting part. For example, when the mounting part has an elongated shape the inner surface of the tip framework is shaped to fit this elongated shape. Different means for holding the tip in place at the mounting part can be used, such as balls pressed into two sides of the mounting part where the tip framework temporarily engages these balls when the tip is arranged at the mounting part.

A releasable attachment of the tip to the main body of the optical scanner provides the advantage that the tip framework can be cleaned separately allowing for a more rough treatment using a more aggressive cleaning agent for the tip framework than the main body of the scanner, which often is not capable of sustaining a rough cleaning procedure. Most often the main body is only suited for a cleaning procedure involving wiping the main body with a cloth containing a disinfectant.

In some embodiments, the tip is permanently attached to the main body. The optical element can then still be releasable attached to the tip framework such that the mirror can be cleaned separately from the other parts of the scanner and such that the mirror can be replaced when required without having to invest in a new scanner.

Disclosed is method for cleaning a tip for an optical scanner, wherein the tip comprises a framework and an optical element releseably attached thereto, wherein the method comprises:
 removing the tip from the scanner;
 removing the optical element from the framework of the tip;
 cleaning the tip framework by applying a first cleaning procedure to the framework; and
 cleaning the optical element by applying a second cleaning procedure to the optical element;
 wherein the first cleaning procedure is more aggressive than the second cleaning procedure.

Commonly used cleaning procedures for dental equipment includes disinfection and sterilization.

The sterilization provides an elimination of all microbiological organisms to provide a sterile microbial environment and can involve e.g. steam sterilization, such as autoclaving, chemical sterilization, and/or sterilization by irradiation. Not all materials can withstand a sterilization without being damaged. For example, the chemical sterilization often use rather aggressive chemicals in either gas or liquid phase which can harm the surface of the sterilized object if this surface is not capable of withstanding sterilization. Disinfection of an object uses is a less aggressive procedure and is accordingly not as effective as a sterilization of the object. However since more materials can withstand a high-level disinfection this procedure is often used in dental praxis.

In some embodiments, the first cleaning procedure comprises sterilization. This provides that no live bacteria, viruses etc. are present on the tip framework. Since the framework is the part of the tip which comes into contact with the tissue in the patient's mouth, such as the gums, lips, tongue and teeth, it is highly advantageous that this part is completely void of transmissible agents such as fungi, bacteria, viruses, spore forms, etc., which can transfer diseases from one patient to the next.

In some embodiments, the second cleaning procedure comprises disinfection, such as high-level disinfection. The high-level disinfection can e.g. be realized using a solution comprising Hydrogen Peroxide optionally in combination with other chemicals. Using a disinfectant on the optical element has the advantage that most of the biological particles present on the optical element are removed while the surface of the optical element is not destroyed which could happen if a sterilization procedure was applied to the optical element.

Since body orifices are relatively small it is preferred that the outer diameter of the tip is as small as possible. However, it is often advantageous for the optical measurements that the cross-sectional diameter of the inner volume of the tip is as large as possible. Therefore the combined wall thickness of the tip framework and the tip-supporting/mounting part of the scanner main body should be at a minimum.

Further it is preferred that condensation on optical elements of the tip due to the humid environment of the body orifice is addressed by heating the optical element to a temperature above the dew point (approximately 35 degrees Celsius).

Disclosed is a tip for a 3D scanner, wherein the tip comprises:

a tip framework, where a first part of the framework comprises a first material and a second part of the framework comprises a second material where both the first and second part form a portion of the outer surface of the framework, and where the ratio between the thermal conductivity of the second material and the thermal conductivity of the first material is 5 or more; and an optical element arranged at said second part of the framework in thermal contact with the second material.

Disclosed is a tip for a 3D scanner for recording topographic characteristics of a surface of a body orifice, wherein the tip comprises:

a framework having a proximal end for entering the body orifice and a distal end, where the outer surface of the framework in the distal end at least partly is made of a first material and the proximal end comprises a second part made in a second material, where the second part form a portion of the outer surface of the framework, and where the ratio between the thermal conductivity of the second material and the thermal conductivity of the first material is 5 or more; and an optical element arranged at said second part in thermal contact with the second material.

Given the lower thermal conductivity of the first material compared to the that of the second material, the first material will act as a thermal insulator such that when the tip is mounted on a warm tip-supporting portion of the 3D scanner the heat will primarily be transferred to the second part of the tip framework wherefrom it can be transferred to the optical element.

Disclosed is a tip for a 3D scanner for recording topographic characteristics of a surface of a body orifice, wherein the tip comprises:

a framework having a proximal end for entering the body orifice and a distal end, where the distal end is made substantially in a thermal insulating material and the proximal end comprises a part made in a thermal conductive material; and an optical element arranged at said part in thermal contact with the thermal conductive material.

Preferably, the tip framework is capable of withstanding aggressive cleaning procedures, such as sterilization by e.g. autoclave or in a dental washer, i.e. both the first and second materials can withstand such a cleaning.

Disclosed is a 3D scanner for recording topographic characteristics of a surface of a body orifice, wherein the 3D scanner comprises:

a tip comprising a framework having a proximal end for entering the body orifice and a distal end, where the distal end is made substantially in a thermal insulating material and the proximal end comprises a part made in a thermal conductive material, and where an optical element of the tip is arranged at said part in thermal contact with the thermal conductive material;

a main body comprising a tip-supporting portion;

a heater system for heating said optical element, said heater system comprising a source of electromagnetic energy and a receptive element configured for receiving the electromagnetic energy and converting it into heat.

In some embodiments, the tip-supporting portion is at least partly formed in a thermal conductive material, where heat is transferred from the thermal conductive material of the tip-supporting portion to the thermal conductive material in the second part of the tip framework when the tip is arranged at the tip-supporting portion of the main body.

Disclosed is a 3D scanner for recording topographic characteristics of a surface of a body orifice, wherein the 3D scanner comprises:

a main body comprising a tip-supporting portion;

a heater system for heating said optical element, said heater system comprising a source of electromagnetic energy and a receptive element configured for receiving the electromagnetic energy and converting it into heat, where the receptive element is arranged in the main body;

a tip according to one of the embodiments;

where the tip supporting portion and the second material of the second part of the tip framework are in thermal contact such that heat can transferred from the tip supporting portion to the second part and the optical element.

The heat receptive element may be an integrated part of the tip-supporting portion with the generated heat being transferred directly to the second part of the tip framework.

The generated heat can also be generated at another part of the 3D scanner and be provided to tip-supporting portion by thermal conduction. The heat from the tip-supporting portion is transferred to the second part of the tip framework from where it can reach the optical element and heat this to prevent condensation of water vapor.

It is advantageous that the distal part of the tip is substantially made in a material with a lower heat conduction than the second part of the tip framework since this part often is in contact with e.g. the lips during an intra-oral scanning and the heating of this part hence preferably should be kept at a minimum. The use of a poorer heat conductor in the distal end of the tip also provides the advantage that the heating system primarily heats the part of the tip where the optical element is located such that the power consumption of the heating system is kept at a minimum.

In some embodiments, the second part consist of the second material, such that the framework at the second part is made of the second material. In that case the second part extends from the inner to the outer surface of the tip framework. The inner surface can then be brought into contact with the warm tip mounting portion of the 3D scanner such that heat can be transferred directly to the second part where the optical element is arranged.

In some embodiments, the ratio between the thermal conductivity of the second material and the thermal conductivity of the first material is 10 or more, such as 15 or more, such as 25 or more, such as 40 or more, such as 50 or more, such as 75 or more, such as 100 or more, such as 250 or more, such as 500 or more, such as 750 or more, such as 1000 or more.

In some embodiments, the first material is a polymer material. In some embodiments, the first material is a polysulfone. Many polymer materials, like polysulfone, has the advantage of a low thermal conductivity and that they can withstand aggressive cleaning, such as autoclave. Polymer frameworks can also be made thin and low weight.

In some embodiments, the second material is a metal. In some embodiments, the second material is aluminum. Metals in general, and aluminum in particular have the advantage of a high thermal conductivity. Further an aluminum part of the framework can also be made thin and low weight, such that the weight and thickness of the framework is kept at a minimum.

In some embodiments, a coating is applied to the second material at least on the outer surface of the tip framework. The coating may be an anti-corrugation coating ensuring that the tip can be used and cleaned several times without the metal corrugating. In some embodiments, the coating comprises a layer of Teflon or chromium.

In the context of the present invention even when a coating is applied to the surface of the second part, the second part is still considered to form a portion of the outer surface of the framework.

In some embodiments, the first part of the tip framework is forms a distal end of the tip configured for engaging a mounting part of a main body of the 3D scanner and the second part is arranged in a proximal end of the tip.

It is advantageous that the second part of the tip is made in the better heat conducting material since the wall thickness of the tip then can be reduced to a minimum. Any thermal insulating material in the region where the optical element is arranged will only increase the thickness of the tip wall without improving the heat conduction to the optical element.

When the stiffness of the thermal conductive material of the tip-mounting portion of the 3D scanner is sufficiently high the tip-supporting portion may be manufactured solely from this material. This is for example the case when the material is steel from which a stiff tubular structure with wall thickness of less than 0.5 mm can be formed.

Disclosed is an optical scanner comprising electronic components for operating the scanner and/or a heating system for heating an optical element of the scanner, where the scanner comprises a cooling system comprising an air circulation system, where the air circulation system comprises an inlet and an outlet, where the outlet and inlet are separate openings of the air circulation system. The cooling system provides that the scanner does not overheat during operation.

Such an arrangement of the inlet and outlet of the air circulation system provides the advantage that the air exiting the outlet is not mixed with the air sucked into the inlet. In prior art scanners, the same opening in the air circulation system is used as inlet and outlet, such that the air for cooling e.g. the electronics of the scanner is heated already before being sucked into the scanner thus lowering the cooling effect of the air cooling system.

In some embodiments, the inlet and outlet are separated by at least 5 mm, such as by 10 mm, such as by 20 mm or more.

The scanner may be a handheld scanner such as a handheld scanner for intra-oral scanning.

Disclosed is a handheld optical scanner, wherein the scanner comprises:

a main body comprising electronic components at least partly enclosed in a housing of the main body; and an interface unit providing electrical and/communication contact between the electronic components within the housing and electronic components of an external system, where the interface unit is a removable unit configured for mating with the main body in a well-defined relative arrangement in which electrical and/communication contact is established between the electronic components of the main body of and of the external system.

Such a modular design of the 3D scanner provides the advantage that the interface unit easily can be replaced in case a malfunction occurs or in the situation where the user wishes to replace the mounted interface unit with another interface unit.

For example, when the interface unit is based on a cable-connection to the external system, the operator may wish to change to an interface unit providing a wireless-based connection to the external system for a battery driven 3D version of the scanner. Or the operator wishes to change to an interface unit having a longer cable. The external system can e.g. be a computer or console configured for connecting to and powering the 3D scanner.

The interface unit can preferably be arranged in the 3D scanner and be removed therefrom without opening the 3D scanner housing.

The present invention relates to different aspects including the tip, scanner and method described above and in the following, and corresponding tips, scanners and methods, each yielding one or more of the benefits and advantages described in connection with the first mentioned aspect, and each having one or more embodiments corresponding to the embodiments described in connection with the first mentioned aspect and/or disclosed in the appended claims.

EMBODIMENTS

1. A tip for an optical scanner, wherein said tip comprises:
a framework;
an optical element; and
a holding means for releasable attaching the optical element to the framework.

2. The tip according to embodiment 1, wherein the holding means comprises a first part permanently attached to the framework and a second part permanently attached to the optical element, where the first and/or second part comprises a magnetic material such that magnetic interaction between the first and second part provides for the releasable attachment of the optical element to the framework.

3. The tip according to embodiment 2, wherein the magnetic material is comprised in one of said first and second parts and the other of said first and second parts comprises a magnetizable material which is magnetized when the first and second parts are brought together.

4. The tip according to any of embodiments 1, 2 or 3, wherein the holding means comprises one or more confining structures arranged to restrict movement of the optical element.

5. The tip according to the embodiment 4, wherein the one or more confining structures comprise one or more stops and/or a surface or an edge of the framework.

6. The tip according to any one of embodiments 1 to 5, wherein the holding means comprises a constriction, such as a slit, adapted for holding the optical element, such that the optical element is releasable attached to the framework when arranged in said constriction.

7. The tip according to embodiment 6, wherein the constriction comprises a first opening allowing the optical element to enter the constriction and a second opening distal to the first opening, where the dimensions of said second opening and of the optical element is such that the height and/or thickness of the optical element exceeds the corresponding height and/or thickness of the second opening.

8. The tip according to any one of embodiments 1 to 6, wherein the optical element comprises a mirror.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

FIGS. 1B, 2A, 2B, 3A, 3B, 4A and 6D show cross-sectional views of the tip where the tip is seen from the side with a view perpendicular to the longitudinal axis of the tip. The longitudinal axis extending from the distal to the proximal end of the tip.

Figure 1A:
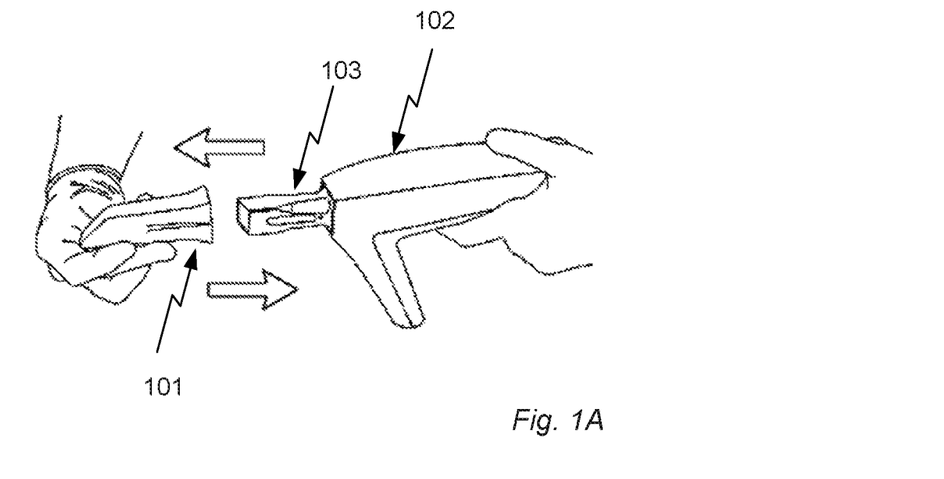
FIGS. 1A and 1B show tip and main body of a 3D scanner.
Figure 1B:
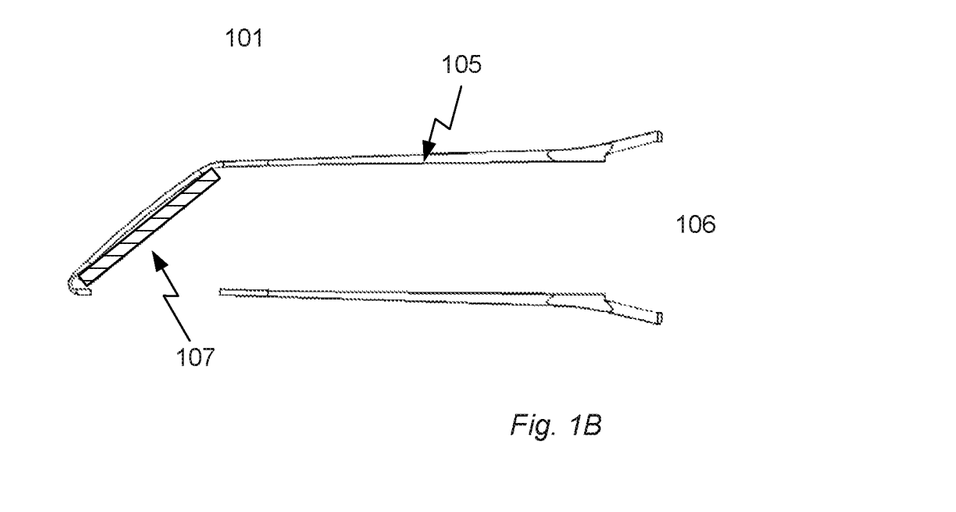

FIGS. 1A and 1B show tip and main body of an optical 3D scanner.

In FIG. 1A is illustrated how the tip 101 can be arranged on the mounting part 103 of the main body 102 of the 3D scanner and be removed therefrom again after the 3D scanner has been used for a scanning. When arranged at the main body, the distal end of the tip is secured at the mounting part while the proximal part of the tip can enter e.g. a patient's mouth in case the 3D scanner is an intra-oral scanner. When used in an intra-oral scanner body fluids potentially carrying disease provoking biological particles, such as various bacteria and viruses, will stick to the tip and unless the tip is cleaned before being used for scanning the next patient, there is a significant risk that these biological particles will be transferred to the next patient. After a scanning the tip must hence be thoroughly cleaned. Here it is an advantage that the tip can be removed from the main body of the scanner since this allows that the tip can be cleaned using a more aggressive cleaning than the main body can withstand.

In FIG. 1B the framework 105 of the tip 101 has an opening at the distal end 106 allowing the tip to be arranged at the main body mounting part. At the proximal end a mirror (the optical element) 107 is arranged such that probe light from the main body can be guided towards an object located outside the tip and light returning from the object can be guided towards an image sensor arranged in the main body.

Figure 2A:
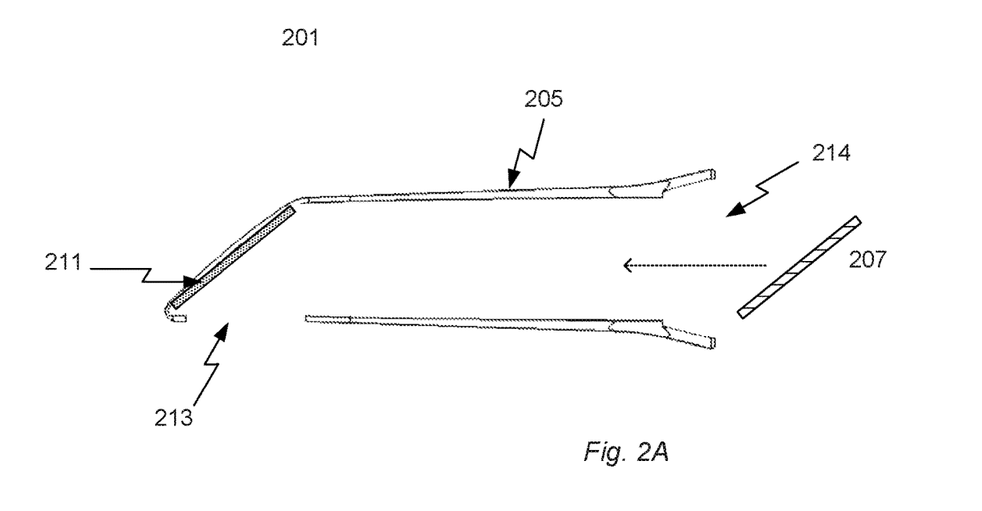
FIGS. 2A and 2B show a schematic of a tip.
Figure 2B:
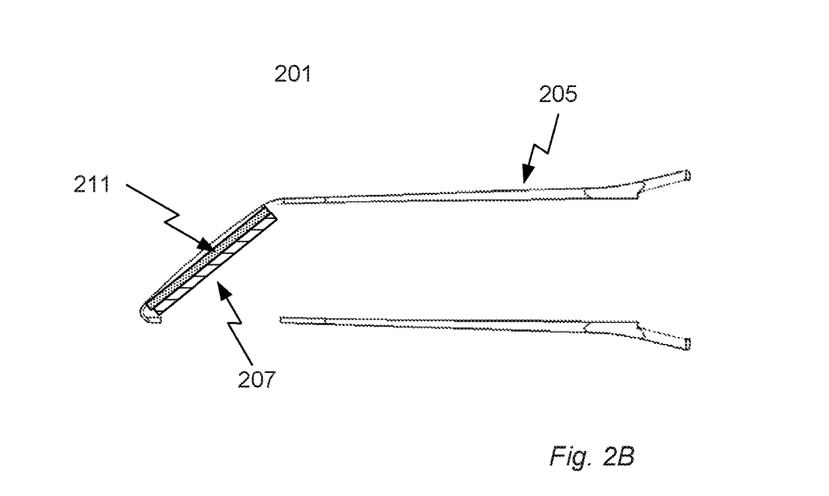

FIGS. 2A and 2B a schematic of a tip for an optical 3D scanner.

The tip 201 has a framework 205 with an opening at the distal end for mounting the tip on a tip-supporting portion of the main body of the 3D scanner. At the proximal end an opening 213 allows for probe light emitted by a light source in the scanner main body to propagate towards the scanned object and light received therefrom to be captured by the imaging system also located in the main body. An opening 214 at the distal end provides that the mirror (the optical element) 207 can enter the inner volume of the tip framework to be arranged at the holding means 211 as illustrated in FIG. 2A. Preferably the mirror 207 is slightly larger than the opening 213 in the proximal end providing that there is less risk of the mirror falling out of the tip in case it should release from the holding means while the scanner is in use. The holding means can e.g. be based on magnetic attraction and/or on mechanical confinement.

In FIG. 2B the mirror 207 is releasable attached to the holding means 211 of the tip 201 and the 3D scanner can be used for scanning e.g. a patient's teeth. The use of a releasable attachment of the mirror to the tip framework provides that the mirror can be separated from the tip framework 205 after use such that it can be cleaned using a more gentle cleaning method than what is used for the framework.

Figure 3A:
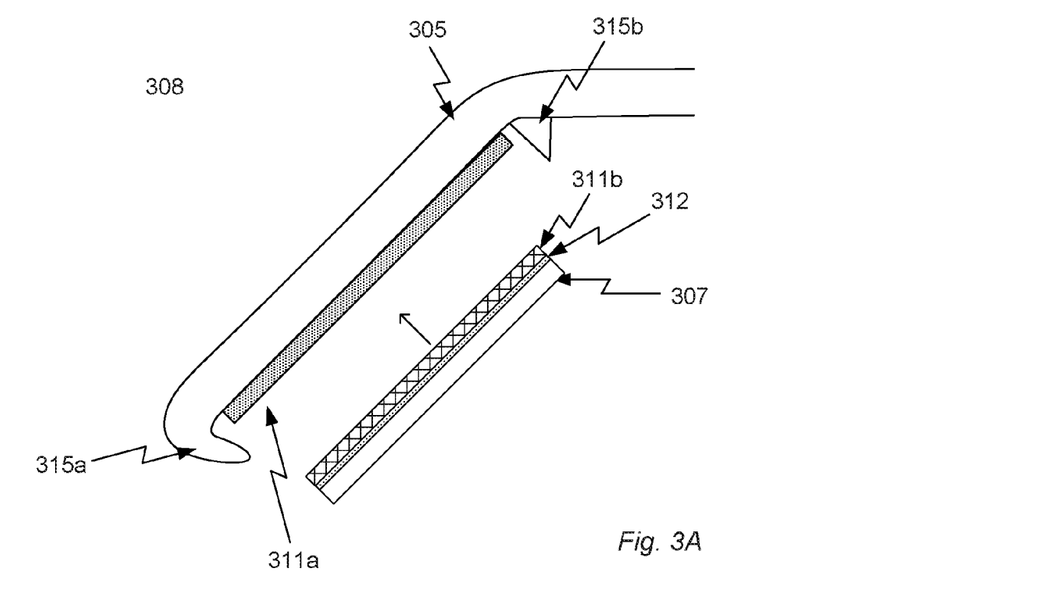
FIGS. 3A and 3B illustrate holding means utilizing magnetic attraction.
Figure 3B:
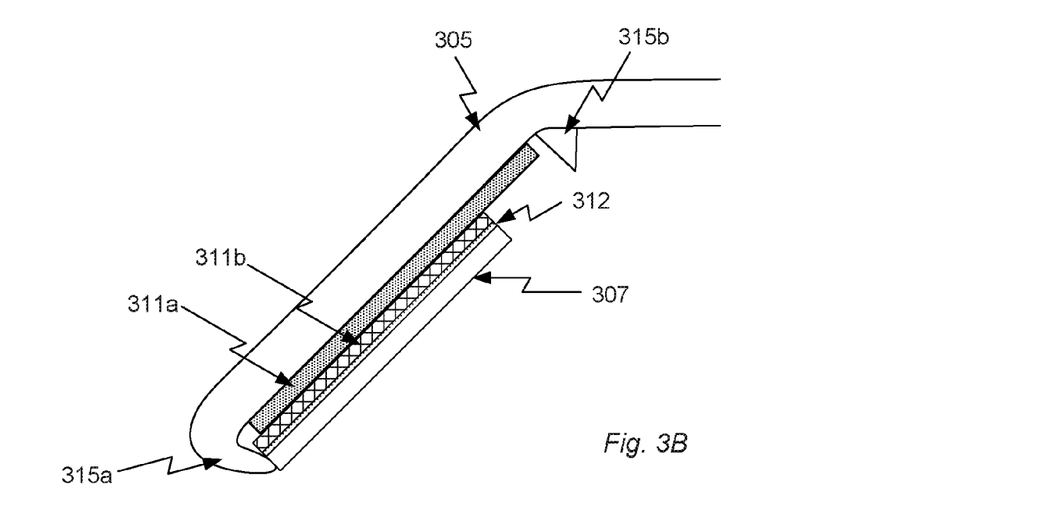

FIGS. 3A and 3B illustrate holding means utilizing magnetic attraction.

The figures show the proximal end 308 of the tip where a 0.5 mm thick sheet of Crofer 22 stainless steel permanently attached to the tip framework 305 forms a first part 311a of a magnetic holding means. The sheet of stainless steel is attached to the framework using ISO10993 certified Loctite 7701 primer and glue.

The second part of the magnetic holding means is formed by a 1 mm thick Neodymium magnet 311b permanently attached to a mirror 307 (the optical element) via an interface plate 312. The interface plate 312 is made of a 0.1 mm thick sheet of Crofer 22 stainless steel and provides that if the mirror breaks the pieces will not fall into the patient's mouth/throat. The mirror, interface plate and magnet are glued together using FDA approved Dow Corning 732 adhesive.

When the Neodymium magnet 311b (second part) and the sheet of stainless steel 311a (first part) are brought together, magnetization of the stainless steel part 311a provides that an attractive magnetic interaction is established between the first and second part providing a releasable attachment of the mirror 307 to the framework 305.

The magnetic interaction between the first part 311a (magnetizable stainless steel) and the second part 311b (Neodymium magnet) provides a force perpendicular to their plane of contact. However the magnetic force does not entirely prevent movement of the second part 311b, and hence of the mirror 307, in the plane of contact with the first part 311a. FIGS. 3A and 3B also illustrate two types of confining structures 315 arranged to restrict movement of the mirror 307 in the plane of contact between the first and second parts of the magnetic holding means 311. One confining structure is formed by the edge 315a at the proximal opening of the framework 305 while the other is a stop 315b provided at the opposite side of the mirror 307. Together these two confining structures 315a, 315b provide that the second part of the magnetic holding means 311b, and hence the mirror 307, cannot slide off the magnetic first part 311a of the holding means whereby the temporary confinement of the mirror 307 at the tip framework 305 is made more secure. This is illustrated in FIG. 3B where the mirror 307 and the second part 311b have moved downwards until they reached the edge 315a at the proximal opening of the framework 305.

FIGS. 4A-4D illustrate a slit-based holding means.

Figure 4A:
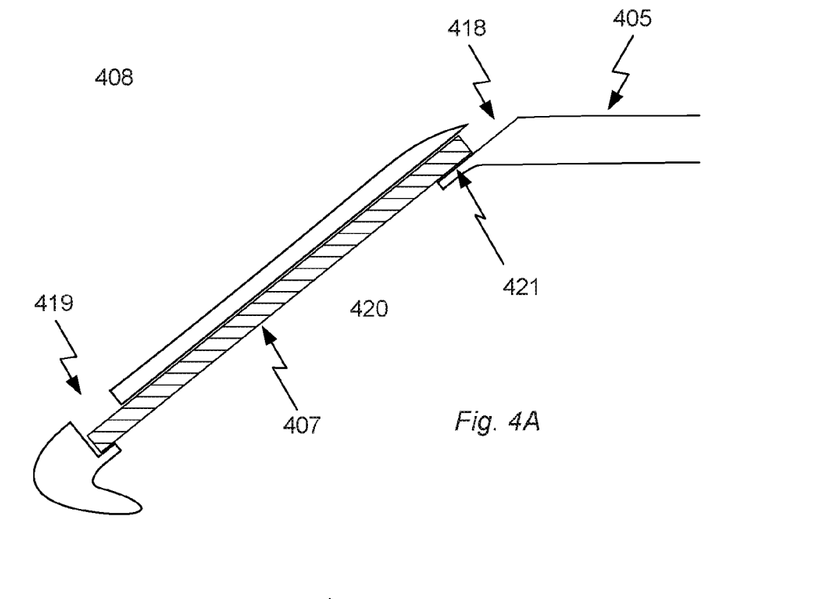
FIGS. 4A-4D illustrate slit-based holding means.
Figure 4B:
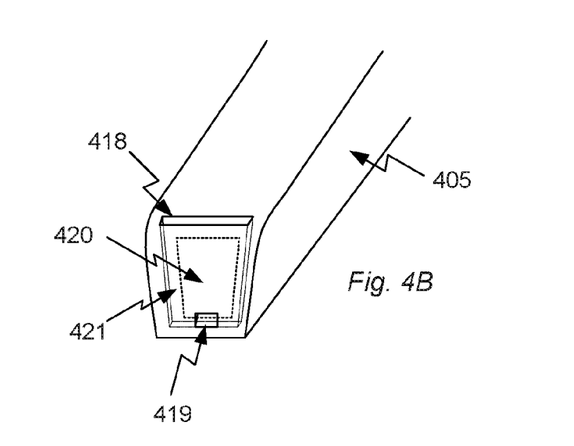

FIGS. 4A and 4B show the proximal end 408 of the tip where a slit defined in the tip framework 405 forms a constriction in which a mirror 407 (the optical element) can be arranged. FIG. 4B is a perspective front view of the proximal end of the tip. The mirror 407 enters the slit through a first opening 418 in the framework 405. A second opening 419 is defined at the opposite end of the slit to allow visual confirmation that the mirror is arranged correctly in the slit and provide a possibility for pushing the mirror out of the slit after scanning. A window 420 is also defined in the framework such that the surface of the mirror is free to reflect e.g. probe light from the main body towards a scanned object. When arranged in the slit, the mirror is supported by the edge 421 surrounding the window 420.

Figure 4C:
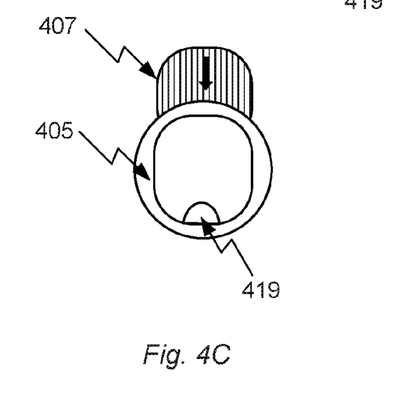
Figure 4D:
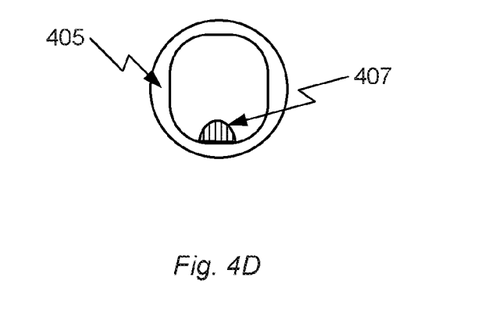

The dimensions of the slit and of the mirror are such that the mirror is held firmly in the slit but still can be removed therefrom without destroying framework or mirror, i.e. the mirror is releasable attached to the framework when arranged in the slit. Alternatively or in addition to the dimensionally provided confinement of the mirror the tip can have a mechanical locking system to ensure that the mirror will not fall out of the tip during scanning. FIGS. 4C and 4D give a front view of the proximal end of the tip and show the second opening 419 in the framework 405 provides information about when the mirror 407 is correctly placed in the slit. In FIG. 4C the mirror cannot be seen in the second opening 419 while in FIG. 4D the mirror 407 can be seen indicating that it is placed correctly.

Figure 5:
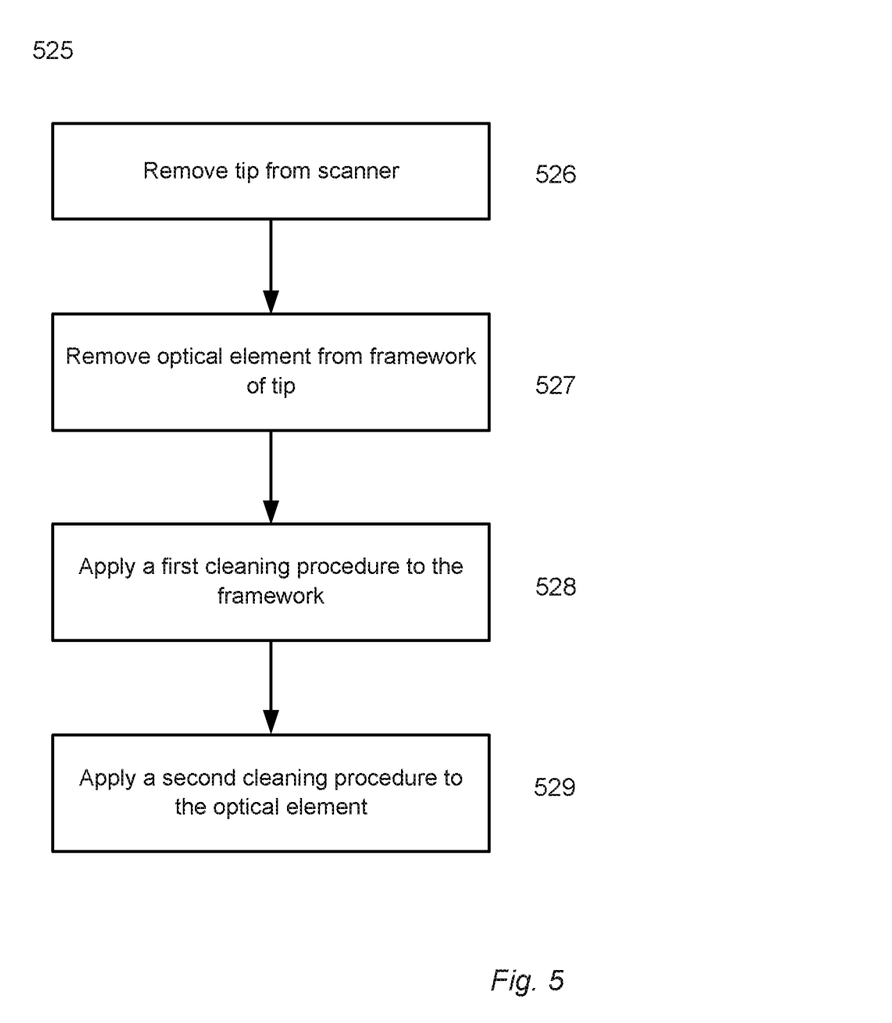
FIG. 5 describes steps of a method for cleaning the tip.

FIG. 5 describes steps of a method for cleaning the tip. When the tip has been used e.g. for intra-oral scanning it must be thoroughly cleaned to avoid the risk of transferring diseases from one patient to another. Initially the tip is removed from the scanner in step 526 and the optical element is removed from the tip framework in step 527. In step 528 a first cleaning procedure comprising sterilization is applied to the framework and in step 529 a second cleaning procedure comprising high-level disinfection is applied to the optical element.

FIGS. 6A-6D show a schematic of a tip design. The framework 605 of the tip is made in a first part 605a and a second part 605b which are manufactured separately and subsequently assembled to form the framework. The tip is adapted for being arranged on a mounting part of the main body of a scanner, where the mounting part at least partly is made of a heat conductor, such as stainless steel, or has a heating element arranged to transfer heat to the tip.

Figure 6A:
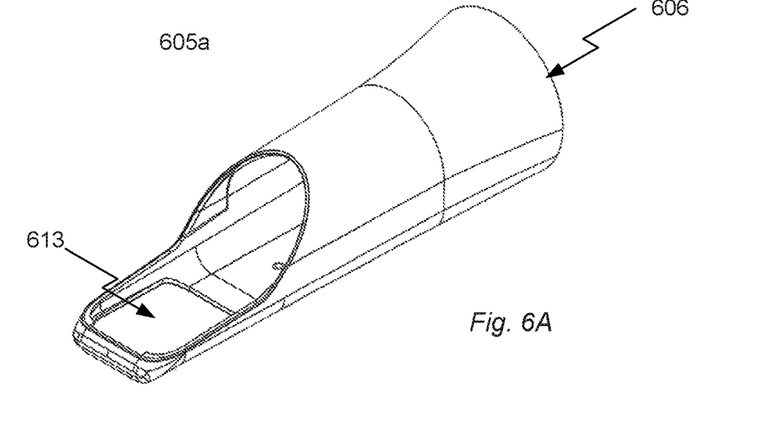
FIGS. 6A-6D show a schematic of a tip design.

The first part 605a illustrated in FIG. 6A is manufactured in Polysulfone (PSU) P1700 using an injection molding process. Polysulfone is a thermoplastic that can withstand repeated sterilization. This is a highly advantageous property since especially this part of the tip comes into contact with the patient's fluids and tissue during a scanning and therefore need to be able to withstand an aggressive cleaning procedure to allow reuse of the tip. Further Polysulfone is a poor heat conductor and hence provide thermal insulation between a heated mounting part and the patient's gums, lips etc. The injection molded first part 605a forms both the distal end and a region of the proximal end, namely the region surrounding the opening 613 at the proximal end of the framework.

Figure 6B:
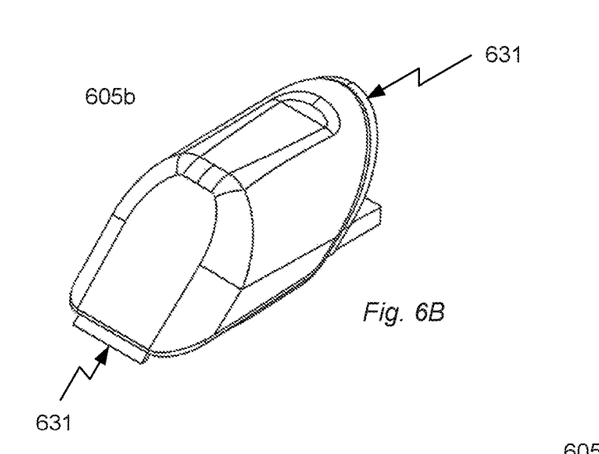
Figure 6C:
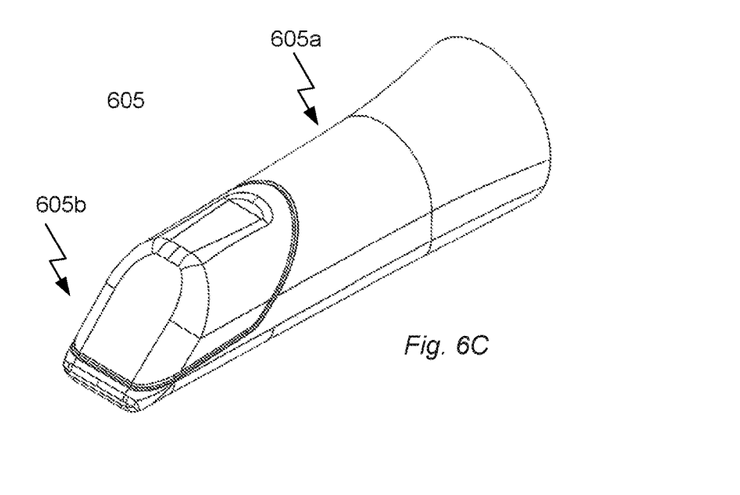

The second part 605b shown in FIG. 6B is made in Aluminum (Aluminum EN AW-6082). A coating including a layer of a fluoropolymer (Teflon®) or a chromium coating is applied to the aluminum material to protect against corrosion due to e.g. autoclave sterilization of the tip. The second part 605b has engaging means 631 shaped for engaging corresponding structures of the first part 605a of the framework to provide the assembly of the first and second parts by mechanical locking. The assembled tip framework is illustrated in FIG. 6C. The first part 605a and the second part 605b together forms the proximal end of the tip framework. In particular the outer surface of the tip framework is formed by the first and second parts.

A mirror (the optical element) is attached to the inner surface of the second part in thermal contact with the Aluminum material such that heat can be transferred from the Aluminum to the mirror.

At relevant temperature for the operation of the tip the thermal conductivity of Polysulfone is 0.25 W/(m*K) and the thermal conductivity of Aluminum is 205 W/(m*K). The ratio between the thermal conductivities is hence 820 and the second part 605b made in Aluminum will guide the heat delivered by mounting part of the scanner to the mirror while only a very small fraction is used for heating the distal part of the tip framework.

Figure 6D:
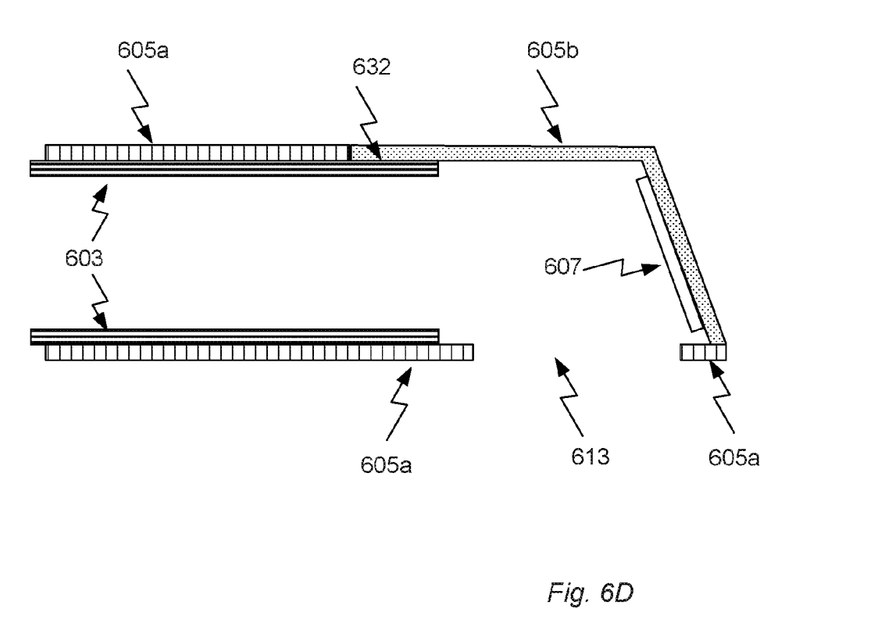

FIG. 6D shows the tip arranged at the mounting part 603 of a main body of a scanner. The mounting part either has a heating element itself or is heated by a heating element in thermal contact with the mounting part. When the tip is arranged at the mounting part, the first part of the tip framework 605a provides thermal insulation between the warm mounting part 603 at the distal end of the tip and at the side of the tip facing the scanned object, i.e. the regions of the first part 605a surrounding the opening 613 at the proximal end of the framework. Instead, heat is transferred in a 632 heat transfer region from the mounting part 603 to the second part of the tip framework 605a where the Aluminum which is a good heat conductor and provides that the mirror 607 attached to the second part of the framework is heated.

For an intra-oral scanner the mirror and hence the second part of the tip framework can be heated to a temperature around 40 degrees Celsius without causing discomfort to the patient. Since the dew point which is around 35 degrees Celsius this is sufficient to prevent condensation on the mirror in the humid environment of the patient's mouth.

The illustrated design has the advantage that the wall thickness of the tip framework can be minimized such that a large cross-sectional diameter of the inner volume of the tip can be obtained while still having a low outer tip diameter.

SELECTED FIGURE REFERENCE NUMBERS

In the Figures the reference numbers are provided in the format according to XYY where "X" is a Figure number indicator showing in which Figure the reference is used and YY is the item number indicator according to the following list.

01 tip
02 main body of scanner
03 mounting part of main body
05 tip framework
05a first part of framework
05b second part of framework
06 distal end of framework
07 optical element
08 proximal end of tip
11 holding means
11a first part of holding means
11b second part of holding means
12 interface plate
13 opening in framework at proximal end of framework
14 opening in framework at distal end of framework
15 confining structure
18 first opening in framework
19 second opening in framework
20 window to optical element
21 supporting edge
31 engaging means
32 heat transfer region Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In tip claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A tip for a 3D scanner, wherein the tip comprises:
    a tip framework, where a first part of the tip framework comprises a first material and a second part of the tip framework comprises a second material, where the first material forms a portion of an outer surface of the tip, where the second material, or an optional coating thereon, forms a portion of the outer surface of the top, and where the ratio between the thermal conductivity of the second material and the thermal conductivity of the first material is 5 or more; and
    an optical element arranged at the second part of the tip framework in thermal contact with the second material.

2. The tip according to claim 1, wherein the second part consists of the second material, such that the tip framework at the second part is made of the second material.

3. The tip according to claim 1, wherein the ratio between the thermal conductivity of the second material and the thermal conductivity of the first material is 10 or more.

4. The tip according to claim 1, wherein the first material is a polymer material.

5. The tip according to claim 4, wherein the first material is a polysulfone.

6. The tip according to claim 1, wherein the second material is a metal.

7. The tip according to claim 6, wherein the second material is aluminum.

8. The tip according to claim 1, wherein the second part comprises the optional coating on the second material at least on the outer surface of the tip.

9. The tip according to claim 8, wherein the coating comprises a layer of Teflon or chromium.

10. The tip according to claim 1, wherein the first part of the tip framework forms a distal end of the tip configured for engaging a mounting part of a main body of the 3D scanner and the second part is arranged in a proximal end of the tip.

11. A tip for a 3D scanner for recording topographic characteristics of a surface of a body orifice, wherein the tip comprises:
    a framework having a proximal end for entering the body orifice and a distal end, where the outer surface of the framework in the distal end at least partly is made of a first material and the proximal end comprises a second part made in a second material, where the second material, or an optional coating thereon, forms a portion of the outer surface of the tip, and where the ratio between the thermal conductivity of the second material and the thermal conductivity of the first material is 5 or more; and
    an optical element arranged at the second part in thermal contact with the second material.

12. The tip according to claim 11, wherein the distal end is made substantially in the first material.

13. A 3D scanner for recording topographic characteristics of a surface of a body orifice, wherein the 3D scanner comprises:
    a main body comprising a tip-supporting portion;
    a heater system for heating said optical element, said heater system comprising a source of electromagnetic energy and a receptive element configured for receiving the electromagnetic energy and converting it into heat, where the receptive element is arranged in the main body;
    a tip according to claim 1;
    where the tip-supporting portion and the second material of the second part of the tip framework are in thermal contact such that heat can transferred from the tip supporting portion to the second part and the optical element.

14. The tip according to claim 1, wherein the ratio between the thermal conductivity of the second material and the thermal conductivity of the first material is 100 or more.

15. The tip according to claim 1, wherein the ratio between the thermal conductivity of the second material and the thermal conductivity of the first material is 500 or more.

* * * * *